(12) United States Patent
Delaney, Jr. et al.

(10) Patent No.: US 12,115,275 B2
(45) Date of Patent: Oct. 15, 2024

(54) BIOCOMPATIBLE POLYISOBUTYLENE-FIBER COMPOSITE MATERIALS AND METHODS

(71) Applicant: Boston Scientific Scimed, Inc., Maple Grove, MN (US)

(72) Inventors: Joseph Thomas Delaney, Jr., Minneapolis, MN (US); Patrick Willoughby, Shoreview, MN (US); David Robert Wulfman, Minneapolis, MN (US); Andrew J. Ro, Plymouth, MN (US); Niraj Gurung, Sauk Rapids, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 822 days.

(21) Appl. No.: 17/179,971

(22) Filed: Feb. 19, 2021

(65) Prior Publication Data

US 2021/0170069 A1    Jun. 10, 2021

Related U.S. Application Data

(62) Division of application No. 15/959,894, filed on Apr. 23, 2018, now Pat. No. 10,925,998.

(Continued)

(51) Int. Cl.
*A61L 27/16*    (2006.01)
*A61L 27/48*    (2006.01)
(Continued)

(52) U.S. Cl.
CPC ............... *A61L 27/16* (2013.01); *A61L 27/48* (2013.01); *C08J 3/246* (2013.01); *C08L 53/00* (2013.01);
(Continued)

(58) Field of Classification Search
CPC ........ A61L 27/48; A61L 2430/20; C08J 3/246
See application file for complete search history.

(56) References Cited

U.S. PATENT DOCUMENTS

| | | |
|---|---|---|
| 4,016,714 A | 4/1977 | Crandall |
| 4,340,091 A | 7/1982 | Davis et al. |

(Continued)

FOREIGN PATENT DOCUMENTS

| | | |
|---|---|---|
| AU | 2016285561 | 10/2020 |
| CN | 1449266 | 10/2003 |

(Continued)

OTHER PUBLICATIONS

"Non-Final Office Action," for U.S. Appl. No. 17/094,206 mailed Jan. 20, 2023 (55 pages).

(Continued)

*Primary Examiner* — Bruce E Snow
(74) *Attorney, Agent, or Firm* — Pauly, DeVries Smith & Deffner LLC (57) ABSTRACT

Aspects herein relate to biocompatible polyisobutylene-fiber composite materials and related methods. In one aspect a biocompatible composite material is included. The biocompatible composite material can include a network of fibers comprising one or more polymers to form a substrate and a continuous polyisobutylene matrix that is non-porous and completely surrounds the electrospun fibers. Other aspects are included herein.

16 Claims, 4 Drawing Sheets

Related U.S. Application Data (60) Provisional application No. 62/489,655, filed on Apr. 25, 2017.

(51) Int. Cl.
    *C08J 3/24* (2006.01)
    *C08L 53/00* (2006.01)
    *D01D 5/00* (2006.01)
    *D01D 5/098* (2006.01)

(52) U.S. Cl.
    CPC ........... *D01D 5/0023* (2013.01); *D01D 5/003* (2013.01); *D01D 5/0985* (2013.01); *A61L 2430/20* (2013.01); *C08J 2323/18* (2013.01); *C08J 2323/22* (2013.01); *C08J 2337/00* (2013.01); *C08J 2479/02* (2013.01); *C08L 2203/02* (2013.01); *D10B 2509/06* (2013.01)

(56) References Cited

U.S. PATENT DOCUMENTS

| | | | |
|---|---|---|---|
| 4,731,074 A | 3/1988 | Rousseau et al. |
| 4,753,652 A | 6/1988 | Langer et al. |
| 4,778,461 A | 10/1988 | Pietsch et al. |
| 5,294,401 A | 3/1994 | Hagiwara |
| 5,296,292 A | 3/1994 | Butters |
| 5,476,507 A | 12/1995 | Wakabayashi et al. |
| 5,674,286 A | 10/1997 | D'Alessio et al. |
| 5,679,299 A | 10/1997 | Gilbert et al. |
| 5,688,597 A | 11/1997 | Kohno |
| 5,740,051 A | 4/1998 | Sanders, Jr. et al. |
| 5,843,158 A | 12/1998 | Lenker et al. |
| 6,165,215 A | 12/2000 | Rottenberg et al. |
| 6,726,715 B2 | 4/2004 | Sutherland |
| 6,953,332 B1 | 10/2005 | Kurk et al. |
| 7,335,264 B2 | 2/2008 | Austin et al. |
| 7,517,353 B2 | 4/2009 | Weber |
| 7,521,296 B2 | 4/2009 | Wood et al. |
| 7,615,335 B2 | 11/2009 | Shelnut et al. |
| 7,786,670 B2 | 8/2010 | Veres et al. |
| 7,988,900 B2 | 8/2011 | Beith |
| 8,043,551 B2 | 10/2011 | Heim et al. |
| 8,324,290 B2 | 12/2012 | Desai et al. |
| 8,361,144 B2 | 1/2013 | Fish et al. |
| 8,529,934 B2 | 9/2013 | Desai et al. |
| 8,590,747 B2 | 11/2013 | Keller |
| 8,845,580 B2 | 9/2014 | Gellman et al. |
| 8,864,816 B2 | 10/2014 | Flanagan et al. |
| 8,945,212 B2 | 2/2015 | Bruchman et al. |
| 8,975,372 B2 | 3/2015 | Ju et al. |
| 9,056,006 B2 | 6/2015 | Edelman et al. |
| 9,074,318 B2 | 7/2015 | Chou et al. |
| 9,145,627 B2 | 9/2015 | Wilson et al. |
| 9,205,172 B2 | 12/2015 | Leonard Neethling et al. |
| 9,216,082 B2 | 12/2015 | Von Segesser et al. |
| 9,255,929 B2 | 2/2016 | Jiang et al. |
| 9,481,949 B2 | 11/2016 | Zhang et al. |
| 9,554,900 B2 | 1/2017 | Bruchman et al. |
| 9,615,919 B2 | 4/2017 | Marissen |
| 9,737,400 B2 | 8/2017 | Fish et al. |
| 9,814,572 B2 | 11/2017 | Edelman et al. |
| 9,944,529 B2 | 4/2018 | Zhang et al. |
| 9,987,130 B2 | 6/2018 | Weber |
| 10,195,023 B2 | 2/2019 | Wrobel |
| 10,299,915 B2 | 5/2019 | Edelman et al. |
| 10,314,696 B2 | 6/2019 | Wulfman et al. |
| 10,368,982 B2 | 8/2019 | Weber et al. |
| 10,413,403 B2 | 9/2019 | Boden et al. |
| 10,426,609 B2 | 10/2019 | Edelman et al. |
| 10,433,955 B2 | 10/2019 | Edelman et al. |
| 10,433,959 B2 | 10/2019 | Levi et al. |
| 10,716,671 B2 | 7/2020 | Eppihimer et al. |
| 10,874,843 B2 | 12/2020 | Adenusi et al. |
| 10,925,998 B2 | 2/2021 | Delaney, Jr. et al. |
| 11,045,312 B2 | 6/2021 | Flaction et al. |
| 11,304,798 B2 | 4/2022 | Wulfman |
| 11,559,394 B2 | 1/2023 | Weber et al. |
| 2001/0025196 A1 | 9/2001 | Chinn et al. |
| 2002/0082689 A1 | 6/2002 | Chinn et al. |
| 2003/0055496 A1 | 3/2003 | Cai et al. |
| 2003/0078652 A1 | 4/2003 | Sutherland |
| 2003/0097175 A1 | 5/2003 | O'Connor et al. |
| 2003/0171802 A1 | 9/2003 | Wilder et al. |
| 2003/0183982 A1 | 10/2003 | Jansen et al. |
| 2003/0225447 A1 | 12/2003 | Majercak et al. |
| 2004/0015233 A1 | 1/2004 | Jansen |
| 2004/0022939 A1 | 2/2004 | Kim et al. |
| 2004/0088046 A1 | 5/2004 | Speziali |
| 2004/0122515 A1 | 6/2004 | Chu |
| 2005/0228486 A1 | 10/2005 | Flagle et al. |
| 2005/0239508 A1 | 10/2005 | Schwarz et al. |
| 2006/0171985 A1 | 8/2006 | Richard et al. |
| 2006/0190074 A1 | 8/2006 | Hill et al. |
| 2007/0118210 A1 | 5/2007 | Pinchuk |
| 2007/0144124 A1 | 6/2007 | Schewe et al. |
| 2007/0232169 A1 | 10/2007 | Strickler et al. |
| 2007/0254005 A1 | 11/2007 | Pathak et al. |
| 2008/0045420 A1 | 2/2008 | Karagianni et al. |
| 2009/0041978 A1 | 2/2009 | Sogard et al. |
| 2009/0054969 A1 | 2/2009 | Salahieh et al. |
| 2009/0117334 A1 | 5/2009 | Sogard et al. |
| 2009/0149673 A1 | 6/2009 | Zhang et al. |
| 2009/0155335 A1 | 6/2009 | O'Shaughnessey et al. |
| 2009/0324679 A1 | 12/2009 | Ippoliti et al. |
| 2010/0023104 A1 | 1/2010 | Desai et al. |
| 2010/0179298 A1 | 7/2010 | Faust et al. |
| 2010/0249922 A1 | 9/2010 | Li et al. |
| 2011/0022160 A1 | 1/2011 | Flanagan et al. |
| 2011/0045030 A1 | 2/2011 | Desai et al. |
| 2011/0208299 A1 | 8/2011 | Marissen |
| 2011/0305898 A1 | 12/2011 | Zhang et al. |
| 2012/0101567 A1 | 4/2012 | Jansen |
| 2012/0122359 A1 | 5/2012 | Lee et al. |
| 2012/0172978 A1 | 7/2012 | Dumontelle |
| 2012/0258313 A1 | 10/2012 | Wen et al. |
| 2012/0290082 A1 | 11/2012 | Quint et al. |
| 2013/0150957 A1 | 6/2013 | Weber et al. |
| 2013/0211508 A1 | 8/2013 | Lane et al. |
| 2013/0274874 A1 | 10/2013 | Hammer et al. |
| 2014/0005771 A1 | 1/2014 | Braido et al. |
| 2014/0005772 A1* | 1/2014 | Edelman .................. A61L 27/34 29/890.12 |
| 2014/0018440 A1 | 1/2014 | Boden |
| 2014/0081414 A1 | 3/2014 | Hall et al. |
| 2014/0088716 A1 | 3/2014 | Zubok et al. |
| 2014/0163671 A1 | 6/2014 | Bruchman et al. |
| 2014/0180402 A1 | 6/2014 | Bruchman et al. |
| 2014/0322512 A1 | 10/2014 | Pham et al. |
| 2015/0005869 A1 | 1/2015 | Soletti et al. |
| 2015/0182332 A1 | 7/2015 | Edelman et al. |
| 2015/0265392 A1 | 9/2015 | Flanagan et al. |
| 2016/0296322 A1 | 10/2016 | Edelman |
| 2016/0296323 A1* | 10/2016 | Wulfman ................ A61L 27/18 |
| 2016/0296325 A1 | 10/2016 | Edelman |
| 2016/0354201 A1 | 12/2016 | Keogh |
| 2017/0000610 A1 | 1/2017 | Eppihimer et al. |
| 2017/0014227 A1 | 1/2017 | Boden et al. |
| 2017/0071729 A1 | 3/2017 | Wrobel |
| 2017/0156854 A1 | 6/2017 | Hammer |
| 2017/0231758 A1 | 8/2017 | Bruchman et al. |
| 2017/0266350 A1 | 9/2017 | Jiang et al. |
| 2017/0333185 A1 | 11/2017 | Weber et al. |
| 2018/0049861 A1 | 2/2018 | Mitchell et al. |
| 2018/0049869 A1 | 2/2018 | Edelman et al. |
| 2018/0206982 A1 | 7/2018 | Haivatov et al. |
| 2018/0263765 A1 | 9/2018 | Flaction |
| 2018/0303972 A1 | 10/2018 | Delaney, Jr. et al. |
| 2019/0125527 A1 | 5/2019 | Binetti et al. |
| 2019/0262131 A1 | 8/2019 | Wulfman et al. |
| 2019/0350703 A1 | 11/2019 | Weber et al. |

(56) References Cited

U.S. PATENT DOCUMENTS

| | | | |
|---|---|---|---|
| 2021/0154006 A1 | 5/2021 | Humair et al. | |
| 2021/0236688 A1 | 8/2021 | Wagner et al. | |

FOREIGN PATENT DOCUMENTS

| | | |
|---|---|---|
| CN | 1621424 | 6/2005 |
| CN | 1647777 | 8/2005 |
| CN | 1874799 | 12/2006 |
| CN | 101128225 | 2/2008 |
| CN | 101437663 | 5/2009 |
| CN | 101505723 | 8/2009 |
| CN | 101690683 | 4/2010 |
| CN | 102602083 | 7/2012 |
| CN | 103109330 | 5/2013 |
| CN | 103628147 | 3/2014 |
| CN | 103702636 | 4/2014 |
| CN | 104203151 | 12/2014 |
| CN | 104220104 | 12/2014 |
| CN | 104674578 | 6/2015 |
| CN | 104780952 | 7/2015 |
| CN | 106084094 | 11/2016 |
| CN | 107405426 | 11/2017 |
| CN | 107847321 | 3/2018 |
| CN | 108024857 | 11/2019 |
| CN | 110494170 | 11/2019 |
| CN | 107427366 | 9/2020 |
| CN | 107735052 | 10/2020 |
| CN | 109475409 | 2/2021 |
| EP | 0331345 | 9/1989 |
| EP | 3280357 | 2/2018 |
| EP | 3280358 | 2/2018 |
| EP | 3322382 | 5/2018 |
| EP | 3349693 | 7/2018 |
| EP | 2866847 | 8/2018 |
| EP | 3457989 | 3/2019 |
| EP | 3316818 | 5/2019 |
| EP | 3615097 | 3/2020 |
| JP | S54090897 | 7/1979 |
| JP | S58133318 | 9/1983 |
| JP | H01310659 | 12/1989 |
| JP | 05237140 | 9/1993 |
| JP | H0654868 | 3/1994 |
| JP | 2008531117 | 8/2008 |
| JP | 2011147790 | 8/2011 |
| JP | 2012500074 | 1/2012 |
| JP | 2013502495 | 1/2013 |
| JP | 2013144009 | 7/2013 |
| JP | 2018516610 | 6/2018 |
| JP | 2018516617 | 6/2018 |
| JP | 2018521765 | 8/2018 |
| JP | 2018523503 | 8/2018 |
| JP | 2018527098 | 9/2018 |
| JP | 2020517368 | 6/2020 |
| JP | 6778693 | 10/2020 |
| JP | 6778702 | 10/2020 |
| WO | 0224119 | 3/2002 |
| WO | 02074201 | 9/2002 |
| WO | 2004080346 | 2/2005 |
| WO | 2005039664 | 5/2005 |
| WO | 2006000763 | 1/2006 |
| WO | 2006091382 | 8/2006 |
| WO | 2008097592 | 8/2008 |
| WO | 2009038761 | 3/2009 |
| WO | 2010020660 | 2/2010 |
| WO | 2010048281 | 4/2010 |
| WO | 2014008207 | 1/2014 |
| WO | 2014143866 | 9/2014 |
| WO | 2014149319 | 9/2014 |
| WO | 2014158444 | 10/2014 |
| WO | 2014163795 | 10/2014 |
| WO | 2016025945 | 2/2016 |
| WO | 2016164197 | 10/2016 |
| WO | 2016164209 | 10/2016 |
| WO | 2017004035 | 1/2017 |
| WO | 2017011392 | 1/2017 |
| WO | 2017048575 | 3/2017 |
| WO | 2017200920 | 11/2017 |
| WO | 2018200378 | 11/2018 |
| WO | 2019210059 | 10/2019 |

OTHER PUBLICATIONS

"Notice of Allowance," for U.S. Appl. No. 16/526,150 mailed Sep. 28, 2022 (12 pages).

"Response to Communication Pursuant to Rules 161(1) and 162 EPC," for European Patent Application No. 20815764.4 filed Jan. 17, 2023 (11 pages).

"Rejection Decision," for Chinese patent application No. 201880024683.0 mailed Apr. 15, 2022 (8 pages) with English Summary.

"Response to Communication Pursuant to Article 94(3) EPC," for European Patent Application No. 18723271.5 filed Jun. 23, 2022 (11 pages).

"Response to Non-Final Rejection," mailed on Mar. 9, 2022 for U.S. Appl. No. 16/526,150, submitted via EFS-Web on Jun. 9, 2022, 8 pages.

Aksoy, Ayse E. et al., "Surface Modification of Polyurethanes with Covalent Immobilization of Heparin," Macromolecular Symposia, vol. 269, Issue 1, pp. 145-153, Aug. 2008 (9 pages).

Alferiev, Ivan et al., "Prevention of polyurethane valve cusp calcification with covalently attached bisphosphonate diethylamino moieties," J Biomed Mater Res 66A: 385-395, 2003 (11 pages).

Athappan, Ganesh et al., "Influence of Transcatheter Aortic Valve Replacement Strategy and Valve Design on Stroke After Transcatheter Aortic Valve Replacement: A Meta-Analysis and Systematic Review of Literature," J Am Coll Cardiol. 2014;63(20):2101-2110 (10 pages).

Barkoula, Nektaria-Marianthi et al., "Processing of Single Polymer Composites Using the Concept of Constrained Fibers," Polymer Composites, 2005, 26: p. 114-120 (7 pages).

Bastiaansen, Cees W. et al., "Melting Behavior of Gelspun-Drawn Polyolefins," Makromol. Chem., Macromol. Symp., 1989. 28: p. 73-84 (12 pages).

Bates, Frank S. et al., "Multiblock Polymers: Panacea or Pandora's Box?," Science, 2012, 336:434-440 (7 pages).

Berkland, Cory et al., "Controlling surface nano-structure using flow-limited field-injection electrostatic spraying (FFESS) of poly(D,L-lactide-co-glycolide)," Biomaterials (2004) 25: 5649-5658 (10 pages).

Bernacca, Gillian M. et al., "Mechanical and morphological study of biostable polyurethane heart valve leaflets explanted from sheep," J Biomed Mater Res 61:138-145, 2002 (8 pages).

Bhattacharyya, D. et al., "Polyamide 6 single polymer composites," eXPRESS Polym. Lett., 2009. 3(8): p. 525-532 (8 pages).

Cacciola, G. et al., "A Synthetic Fiber-Reinforced Stentless Heart Valve," Journal of Biomechanics, Jan. 1, 2000, pp. 653-658, XP055284947, Retrieved from the Internet: URL:http://ac.els-cdn.com.

Cacciola, G. et al., "A Three-Dimesional Mechanical Analysis of a Stentless Fibre-Reinforced Aortic Valve Prosthesis," Journal of Biomechanics, Jan. 1, 2000, pp. 521-530, XP055284955, Retrieved from the Internet: URL:http://ac.els-cdn.com.

Charles, Lyndon F. et al., "Self-reinforced composites of hydroxyapatite-coated PLLA fibers: fabrication and mechanical characterization," J. Mech. Behav. Biomed. Mater., 2013. 17: p. 269-277 (9 pages).

Claiborne, Thomas E. et al., "In Vitro Evaluation of a Novel Hemodynamically Optimized Trileaflet Polymeric Prosthetic Heart Valve," Journal of Biomechanical Engineering 2013, vol. 135 (8 pages).

De Yoreo, James J. et al., "Principles of Crystal Nucleation and Growth," Biomineralization, Mineral Soc. Am., Washington, DC, 2003, pp. 57-93 (37 pages).

"Decision of Final Rejection," for China Patent Application No. 201380044842.0, mailed Apr. 7, 2017 (18 pages) with Summary.

"Decision of Rejection," for Chinese Patent Application No. 201380044842.0 mailed Sep. 17, 2019 (9 pages) with English Summary.

(56) References Cited

OTHER PUBLICATIONS

Dencheva, Nadya et al., "Structure-properties relationship in single polymer composites based on polyamide 6 prepared by in-mold anionic polymerization," J. Mater. Sci., 2013. 48(20): p. 7260-7273 (14 pages).
Duhovic, Miro P. et al., "Polyamide 66 polymorphic single polymer composites," Open Macromol. J., 2009. 3: p. 37-40. (4 pages).
Fabreguette, et al., "X-ray mirrors on flexible polymer substrates fabricated by atomic layer deposition," Thin Solid Films 515: 7177-7180 (2007), 5 pages.
Fabreguette, Francois H. et al., "Ultrahigh x-ray reflectivity from W/Al2O3 multilayers fabricated using atomic layer deposition," Applied Physics Letters 88: 013166 (2006), 3 pages.
Fakirov, Stoyko "Nano- and Microfibrillar Single-Polymer Composites: A Review," Macromol. Mater. Eng., 2013. 298(1): p. 9-32 (24 pages).
Feng, Yakai et al., "Surface modification of polycarbonate urethane by covalent linkage of heparin with a PEG spacer," Transactions of Tianjin University, Feb. 2013, vol. 19, Issue 1, pp. 58-65 (8 pages).
File History for U.S. Appl. No. 15/959,894 downloaded Mar. 19, 2021 (329 pages).
File History for European Patent Application No. 13739321.1 downloaded Mar. 22, 2021 (377 pages).
File History for European Patent Application No. 16715218.0 downloaded Mar. 22, 2021 (245 pages).
File History for European Patent Application No. 16715724.7 downloaded Apr. 6, 2021 (251 pages).
File History for U.S. Appl. No. 15/797,394 downloaded Mar. 30, 2021 (288 pages).
File History for U.S. Appl. No. 14/656,044 downloaded Mar. 30, 2021 (372 pages).
File History for U.S. Appl. No. 13/932,968 downloaded Mar. 30, 2021 (288 pages).
File History for U.S. Appl. No. 15/082,239 downloaded Mar. 30, 2021 (301 pages).
File History for European Patent Application No. 16736720.0 downloaded Mar. 30, 2021 (256 pages).
File History for European Patent Application No. 16741492.9 downloaded Mar. 30, 2021 (217 pages).
File History for European Patent Application No. 16766455.6 downloaded Mar. 30, 2021 (249 pages).
File History for European Patent Application No. 17725140.2 downloaded Mar. 30, 2021 (120 pages).
File History for European Patent Application No. 18723271.5 downloaded Mar. 30, 2021 (122 pages).
File History for U.S. Appl. No. 16/413,104 downloaded Mar. 31, 2021 (163 pages).
File History for U.S. Appl. No. 15/082,382 downloaded Mar. 31, 2021 (275 pages).
File History for U.S. Appl. No. 15/082,293 downloaded Mar. 31, 2021 (229 pages).
File History for U.S. Appl. No. 15/193,794 downloaded Mar. 31, 2021 (902 pages).
File History for U.S. Appl. No. 15/205,098 downloaded Mar. 31, 2021 (258 pages).
File History for U.S. Appl. No. 15/257,211 downloaded Mar. 31, 2021 (224 pages).
File History for U.S. Appl. No. 16/526,150 downloaded Mar. 31, 2021 (118 pages).
File History for U.S. Appl. No. 15/55,176 downloaded Mar. 31, 2021 (201 pages).
"First Examination Report," for Australian Patent Application No. 2016285561 mailed Mar. 12, 2020 (3 pages).
"First Office Action," for Chinese Patent Application No. 201380044842.0 mailed Dec. 18, 2015 (15 pages) with English Translation.
"First Office Action," for Chinese Patent Application No. 20160036250.8 mailed Nov. 2, 2018 (11 pages) with English Summary.
"First Office Action," for Chinese Patent Application No. 201680018663.3 mailed Mar. 16, 2020 (12 pages) with English Summary.
"First Office Action," for Chinese Patent Application No. 201680018700.0 mailed Nov. 2, 2018 (12 pages) with English Summary.
"First Office Action," for Chinese Patent Application No. 201680040898.2 mailed Feb. 28, 2019, 17 pages, with English summary.
"First Office Action," for Chinese Patent Application No. 201680053293.7 mailed Mar. 5, 2019 (7 pages) with English Summary.
"First Office Action," for Chinese Patent Application No. 201780042303.1 mailed Mar. 26, 2020 (16 pages) with English Summary.
Gallocher, "Durability Assessment of Polymer Trileaflet Heart Valves," FIU Electronic Theses and Dissertations, Paper 54, 2007 (237 pages).
Généreux, Philippe et al., "Vascular Complications After Transcatheter Aortic Valve Replacement: Insights from the PARTNER Trial," J Am Coll Cardiol. 2012;60(12):1043-1052 (10 pages).
George, "Final Report—Fabrication of Nanolaminates with Ultrathin Nanolayers Using Atomic Layer Deposition: Nucleation & Growth Issues," AFOSR Grant No. FA9550-01-1-0075 Feb. 2009 (36 pages).
"Glycosaminoglycan," Wikipedia, posted on or before Oct. 16, 2004, retrieved Feb. 13, 2014, http://en.wikipedia.org/wiki/Glycosaminoglycan, 6 pages.
Gong, Ying et al., "Polyamide single polymer composites prepared via in situ anionic polymerization of s-caprolactam," Composites, Part A, 2010. 41A(8): p. 1006-1011 (6 pages).
Gong, Ying et al., "Single polymer composites by partially melting recycled polyamide 6 fibers: preparation and characterization," J. Appl. Polym. Sci., 2010. 118(6): p. 3357-3363 (7 pages).
Goyal, R. K. et al., "High performance polymer composites on PEEK reinforced with aluminum oxide," J. Appl. Polym. Sci., 2006. 100(6): p. 4623-4631 (9 pages).
Groner, M. D. et al., "Gas Diffusion Barriers on Polymers Using Al2O3 Atomic Layer Deposition," Applied Physics Letters 88, 051907, 2006 (3 pages).
Han, Dong K. et al., "In vivo biostability and calcification-resistance of surface-modified PU-PEO-SO3," Journal of Biomedical Materials Research, vol. 27, 1063-1073, 1993 (11 pages).
Hass, D. D. et al., "Reactive vapor deposition of metal oxide coatings," Surface and Coatings Technology 146-147 (2001) 85-93, 9 pages.
Hine, P.J. et al., "High stiffness and high impact strength polymer composites by hot compaction of oriented fibers and tapes.," in Mechanical Properties of Polymers Based on Nanostructure and Morphology, CRC Press, 2005 (45 pages).
Hine, P.J. et al., "Hot compaction of woven nylon 6,6 multifilaments," J. Appl. Polym. Sci., 2006. 101(2): p. 991-997 (7 pages).
Hine, P.J. et al., "Hot Compaction of Woven Poly(ethylene terephthalate) Multifilaments," J. Appl. Polym. Sci., 2004. 91(4): p. 2223-2233 (11 pages).
Hine, P.J. et al., "Hybrid carbon fibre/nylon 12 single polymer composites," Composites Part A: Applied Science and Manufacturing 65 (2014) (17 pages).
"International Preliminary Report on Patentability," For International Application No. PCT/US2013/048976 mailed Jan. 6, 2015 (9 pages).
"International Preliminary Report on Patentability," for PCT Application No. PCT/US2016/024614 mailed Oct. 19, 2017 (7 pages).
"International Preliminary Report on Patentability," for PCT Application No. PCT/US2016/024753 mailed Oct. 19, 2017 (7 pages).
"International Preliminary Report on Patentability," for PCT Application No. PCT/US2016/039808 mailed Jan. 11, 2018 (8 pages).
"International Preliminary Report on Patentability," for PCT Application No. PCT/US2016/041757 mailed Jan. 25, 2018 (8 pages).
"International Preliminary Report on Patentability," for PCT Application No. PCT/US2016/050691 mailed Mar. 29, 2018 (9 pages).
"International Preliminary Report on Patentability," for PCT Application No. PCT/US2017/032656 mailed Nov. 29, 2018 (7 pages).

(56) References Cited

OTHER PUBLICATIONS

"International Preliminary Report on Patentability," for PCT Application No. PCT/US2018/028864 mailed Nov. 7, 2019 (7 pages).
"International Search Report & Written Opinion," for International Application No. PCT/US2013/048976, mailed Nov. 19, 2013 (20 pages).
"International Search Report and Written Opinion," for PCT Application No. PCT/EP2020/083331 mailed Feb. 22, 2021 (12 pages).
"International Search Report and Written Opinion," for PCT Application No. PCT/US2016/041757 mailed Oct. 12, 2016 (12 pages).
"International Search Report and Written Opinion," for PCT application No. PCT/US2016/050691 mailed Dec. 19, 2016 (14 pages).
"International Search Report and Written Opinion," for PCT Application No. PCT/US2017/032656 mailed Jul. 21, 2017 (16 pages).
"International Search Report and Written Opinion," for PCT Application No. PCT/US2018/028864 mailed Jul. 30, 2018 (10 pages).
"International Search Report and Written Opinion," for PCT/US2016/024614 mailed Jul. 12, 2016 (13 pages).
"International Search Report and Written Opinion," for PCT/US2016/024753 mailed Jul. 22, 2016 (11 pages).
"International Search Report and Written Opinion," for PCT/US2016/039808 mailed Sep. 26, 2016 (11 pages).
Jen, Shih-Hui et al., "Critical tensile and compressive strains for cracking of al2O3 films grown by atomic layer deposition," Journal of Applied Physics 109, 084305 (2011), 11 pages.
Jen, Shih-Hui et al., "Critical tensile strain and water vapor transmission rate for nanolaminate films grown using al2o3 atomic layer deposition and alucone molecular layer deposition," Applied Physics Letters 101, 234103 (2012), 3 pages.
Jiang, Shaoyi et al., "Ultralow-Fouling, Functionalizable, and Hydrolyzable Zwitterionic Materials and Their Derivatives for Biological Applications," Adv Mater. Mar. 5, 2010;22(9):920-32 (13 pages).
Kalejs, et al., "St. Jude Epic Heart Valve Bioprostheses Versus Native Human and Porcine Aortic Valves—Comparison of Mechanical Properties," Interactive Cardiovascular and Thoracic Surgery 8 (2009) 553-557.
Kalfon-Cohen, Estelle et al., "Microstructure and nematic transition in thermotropic liquid crystalline fibers and their single polymer composites," Polym. Adv. Technol., 2007. 18(9): p. 771-779 (9 pages).
Kang, Jungmee et al., "Polyisobutylene-Based Polyurethanes with Unprecedented Properties and How They Came About," Journal of Polymer Science Part A: Polymer Chemistry, 2011. 49(18): p. 3891-3904 (14 pages).
Khondker, O.A. et al., "Fabrication and mechanical properties of aramid/nylon plain knitted composites," Composites Part A: Applied Science and Manufacturing, 2004. 35(10): p. 1195-1205 (11 pages).
Kim, Nam K. et al., "Nanofibrillar Poly(vinylidene fluoride): Preparation and Functional Properties," Int. J. Polym. Mater. Polym. Biomater., 2014. 63(1): p. 23-32 (10 pages).
Kim, Nam K. et al., "Polymer-Polymer and Single Polymer Composites Involving Nanofibrillar Poly(vinylidene Fluoride): Manufacturing and Mechanical Properties," J. Macromol. Sci., Part B: Phys., 2014. 53(7): p. 1168-1181 (14 pages).
Kuang, Jinghao et al., "Universal Surface-initiated Polymerization of Antifouling Zwitterionic Brushes Using a Mussel Mimetic Peptide Initiator," Langmuir. May 8, 2012; 28(18): 7258-7266 (20 pages).
Lane, Bobby "What Line Should I Use?," Bassmaster.com (www.bassmaster.com/tips/ask-experts-what-line-should-i-use) Apr. 1-7, 2013.
"Liquid-Crystal Polymer," Wikipedia, the Free Encyclopedia <http://en/wikipedia.org/wiki/Liquid-crystal_polymer>, retrieved Jun. 2, 2016 (3 pages).
Liu, et al., "Effect of fiber orientation on the stress distribution within a leaflet of a polymer composite heart valve in the closed position," J of Biomedichanics, 2007, 40:1099-1106 (8 pages).
Mach, H. et al., "Highly Reactive Polyisobutene as a Component of a New Generation of Lubricant and Fuel Additives," Lubrication Science 1999, 11 (2), 175-185 (11 pages).

Madhusha, "Difference between Fluorine and Fluoride," Aug. 9, 2017, PEDIAA.com, pp. 1-8. URL <http://pediaa.com/difference-between-fluorine-and-fluoride/> (8 pages).
Maity, J. et al., "Homocomposites of chopped fluorinated polyethylene fiber with low-density polyethylene matrix," Mater. Sci. Eng., A, 2008. A479(1-2): p. 125-135 (11 pages).
Masoumi, et al., "Trilayered Elastomeric Scaffolds for Engineering Heart Valve Leaflets," Biomaterials. Sep. 2014; 35(27):7774-7785.
Matabola, K. P. et al., "Single polymer composites: a review," Journal of Materials Science, 2009. 44(23): p. 6213-6222 (10 pages).
McKenna, H. A. et al., "Handbook of Fibre Rope Technology," The Textile Institute, Woodhead Publishing Limited, Cambridge England 2004, 1-432.
Medeiros Araujo, Thiago et al., "Liquid crystalline single-polymer short-fibers composites," Composite Interfaces, 2013. 20(4): p. 287-298 (12 pages).
Mitchell, J. "Braided Fishing Lines (Superlines)," Sufix Fishing Lines Product page as it appeared Apr. 5, 2019 (https://sufix.fishing/braided-fishing-lines-superlines), 1-5.
"Notification of Patent Reexamination," for Chinese Patent Application No. 201380044842.0 mailed Feb. 7, 2018 (12 pages) with English summary.
"Office Action," for Japanese Patent Application No. 2017-549776 mailed Dec. 17, 2019 (9 pages) with English Translation.
"Office Action," for Japanese Patent Application No. 2017-549776 mailed Jun. 2, 2020 (4 pages) with English Summary.
"Office Action," for Japanese Patent Application No. 2017552443 mailed Dec. 17, 2019 (14 pages) with English Translation.
"Office Action," for Japanese Patent Application No. 2017-552443 mailed Sep. 15, 2020 (10 pages) with English Translation.
"Office Action," for Japanese Patent Application No. 2017-564627 mailed Jan. 21, 2020 (9 pages) with English Translation.
"Office Action," for Japanese Patent Application No. 2018-501287 mailed Dec. 1, 2020 (9 pages) with English Translation.
"Office Action," for Japanese Patent Application No. 2018513335 mailed Aug. 4, 2020 (5 pages) with English Translation.
"Office Action," for Japanese Patent Application No. 2019-557835 mailed Sep. 8, 2020 (6 pages) with English Translation.
"Office Action," for JP Patent Application No. 2018-501287 mailed Jun. 2, 2020 (6 pages) with English Summary.
Ohri, Rachit et al., "Hyaluronic acid grafting mitigates calcification of glutaraldehyde-fixed bovine pericardium," J Biomed Mater Res 70A: 328-334, 2004 (7 pages).
Raghavan, R. et al., "Nanocrystalline-to-amorphous transition in nanolaminates grown by low temperature atomic layer deposition and related mechanical properties," Applied Physics Letters 100, 191912 (2012), 9 pages.
"Response to First Examination Report," for Australian Patent Application No. 2016285561 filed May 18, 2020 (11 pages).
Rutledge, G.C. et al., "Electrostatic Spinning and Properties of Ultrafine Fibers," National Textile Center Annual Report: Nov. 2001, M01-D22, (10 pages).
Schneider, Tobias et al., "Influence of fiber orientation in electrospun polymer scaffolds on viability, adhesion and differentiation of articular chondrocytes," Clinical Hemorheology and Microcirculation 52 (2012) 325-336 (13 pages).
"Second Office Action," for Chinese Patent Application No. 201380044842.0, mailed Aug. 12, 2016 (16 pages) with summary.
"Second Office Action," for Chinese Patent Application No. 201680018663.3 mailed Dec. 16, 2020 (6 pages) with English Summary.
"Second Office Action," for Chinese Patent Application No. 201680018700.0 mailed Jul. 12, 2019 (11 pages) with English Summary.
"Second Office Action," for Chinese Patent Application No. 201680036250.8 mailed Jul. 11, 2019 (7 pages) with English Summary.
"Second Office Action," for Chinese Patent Application No. 201680040898.2 mailed Nov. 4, 2019 (12 pages), with English Summary.
"Second Office Action," for Japanese Patent Application No. 2019-557835 mailed Mar. 9, 2021 (2 pages) No English Translation.

(56) References Cited

OTHER PUBLICATIONS

Shin, Y. M. et al., "Experimental characterization of electrospinning: the electrically forced jet and instabilities," Polymer 42 (2001) 9955-9967 (13 pages).
Sun, Xiaoli et al., "α and β Interfacial Structures of the iPP/PET Matrix/Fiber Systems," Macromolecules, 2007. 40(23): p. 8244-8249 (6 pages).
Szeghalmi, Adriana et al., "All dielectric hard x-ray mirror by atomic layer deposition," Applied Physics Letters 94, 133111 (2009), 3 pages.
Szilagyi, Imre M. et al., "Review on One-Dimensional Nanostructures Prepared by Electrospinning and Atomic Layer Deposition," INERA Workshop of ISCMP2014, IOP Publishing, Journal of Physics: Conference Series 559, 2014 (13 pages).
"Third Office Action," for Chinese Patent Application No. 201680036250.8 mailed Mar. 2, 2020 (10 pages) with English Summary.
"Third Office Action," for Chinese Patent Application No. 201380044842.0 mailed Dec. 29, 2018 (12 pages), with English translation.
"Third Office Action," for Chinese Patent Application No. 201680018700.0 mailed Feb. 3, 2020 (8 pages) with English Summary.
Tu, Qin et al., "Synthesis of polyethylene glycol- and sulfobetaine-conjugated zwitterionic poly(l-lactide) and assay of its antifouling properties," Colloids and Surfaces B; Biointerfaces 102 (2013) 331-340 (10 pages).
Vesely, et al., "Micromechanics of the Fibrosa and the Ventricularis in Aortic Valve Leaflets," J Biomech. 1992 25(1):101-113.
Vick, Linda W. et al., "Hot compaction and consolidation of polycarbonate powder," Polym. Eng. Sci., 1998. 38(11): p. 1824-1837 (14 pages).
Wang, Qiang et al., "A novel small animal model for biocompatibility assessment of polymeric materials for use in prosthetic heart valves," J Biomed Mater Res 93A: 442-453, 2010 (12 pages).
Wang, Qiang et al., "In-Vivo Assessment of a Novel Polymer (SIBS) Trileaflet Heart Valve," J Heart Valve Dis, Jul. 2010, 19(4):499-505 (7 pages).
Ward, I.M. et al., "Developments in oriented polymers," Plastics, Rubber and Composites, 2004. 33(5): p. 189-194 (6 pages).
Ward, I.M. et al., "Novel composites by hot compaction of fibers," Polym. Eng. Sci., 1997. 37(11): p. 1809-1814 (6 pages).
Wheatley, et al., "Polyurethane: material for the next generation of heart valve prostheses?," Eur J Cardio-Thoracic Surg, 2000, 17:440-448 (11 pages).
"Why Use Superlines?," Berkley-Fishing.com (www.berkley-fishing.com/Berkley-ae-why-use-superlines.html), 1-6.
Yang, Mingjing et al., "Assessing the Resistance to Calcification of Polyurethane Membranes Used in the Manufacture of Ventricles for a Totally Implantable Artificial Heart," J Biomed Mater Res (Appl Biomater) 48: 648-659, 1999 (12 pages).
Yao, Jian et al., "High Strength and High Modulus Electrospun Nanofibers," Fibers 2014; 2:158-187 (30 pages).
Yeh, Shiou-Bang et al., "Modification of Silicone Elastomer with Zwitterionic Silane for Durable Antifouling Properties," Langmuir 2014, 30, 11386-11393 (8 pages).
Zhang, Baoyan et al., "Studies of Novel Segmented Copolyether Polyurethanes," Eur. Polym. J., vol. 34, No. 3-4, pp. 571-575 (1998) (5 pages).
Zhang, Zhiping et al., "Effect of Crosslinking and Grafting by 60Co-γ-ray Irradiation on Carbon Black/Polyethylene Switching Materials and Fluoride Resin System in self-regulating Heating Cables," JAERI-Conf, 2000. 2000-001(JCBSRC '99, the 8th Japan-China Bilateral Symposium on Radiation Chemistry, 1999): p. 202-210 (9 pages).
Zhao, Zeng Hua et al., "Research development of single polymer composite preparation," Gongcheng Suliao Yingyong, 2010. 38(2): p. 81-84, with machine translation (11 pages).
"First Office Action," for Chinese Patent Application No. 201880024683.0 mailed May 28, 2021 (11 pages) with English Summary.
"Non-Final Office Action," for U.S. Appl. No. 16/413,104 mailed Jul. 20, 2021 (74 pages).
"Office Action," for Japanese Patent Application No. 2018-501287 mailed Jun. 15, 2021 (4 pages).
"Response to Communication Pursuant to Article 94(3) EPC," for European Patent Application No. 16715724.7 filed Aug. 9, 2021 (53 pages).
"Communication Pursuant to Article 94(3) EPC," for European Patent Application No. 16715724.7 mailed Apr. 15, 2021 (4 pages).
Fazal, Adnan et al., "UHMWPE fibre-based composites: Prestress-induced enhancement of impact properties," Composites Part B, 2014, vol. 66, pp. 1-6 (12 pages).
"Office Action," for Japanese Patent Application No. 2018-513335 mailed Apr. 6, 2021 (7 pages) with English Translation.
"Notice of Allowance," for U.S. Appl. No. 16/413,104 mailed Dec. 24, 2021 (14 pages).
"Second Office Action," for Chinese Patent Application No. 201880024683.0 mailed Dec. 9, 2021 (9 pages) with English Summary.
"Communication Pursuant to Article 94(3) EPC," for European Patent Application No. 18723271.5 mailed Feb. 16, 2022 (6 pages).
"Non-Final Office Action," for U.S. Appl. No. 16/526,150 mailed Mar. 9, 2022 (61 pages).
"Final Office Action," for U.S. Appl. No. 17/094,205 mailed Aug. 23, 2023 (15 pages).
"Office Action," for Japanese Patent Application No. 2022-529907 mailed Apr. 18, 2023 (12 pages) with English translation.
"Response to Non-Final Rejection," mailed on Jan. 20, 2023 for U.S. Appl. No. 17/094,205, submitted via EFS-Web on Apr. 20, 2023, 8 pages.
"Notification of Reexamination," for Chinese Patent Application No. 201380044842.0 mailed Sep. 26, 2021 (21 pages) with English translation.
"Response to Non-Final Rejection," mailed on Jul. 20, 2021 for U.S. Appl. No. 16/413,104, submitted via EFS-Web on Oct. 19, 2021, 12 pages.
"Decision of Rejection," for Japanese Patent Application No. 2022-529907 mailed Oct. 31, 2023 (10 pages) with English Translation.
"Non-Final Office Action," for U.S. Appl. No. 17/094,205 mailed Jan. 19, 2024 (11 pages).
"Response to Final Rejection," mailed on Aug. 23, 2023, for U.S. Appl. No. 17/094,205, submitted via EFS-Web on Dec. 15, 2023, 8 pages.
"Communication Pursuant to Article 94(3) EPC," for European Patent Application No. 18723271.5 mailed Mar. 18, 2024 (6 pages).
"Response to Non-Final Rejection," mailed on Jan. 19, 2024, for U.S. Appl. No. 17/094,205, submitted via EFS-Web on Apr. 19, 2024, 10 pages.
"Final Office Action," for U.S. Appl. No. 17/094,205 mailed Aug. 15, 2024 (17 pages).
"Response to Communication Pursuant to Article 94(3) EPC," for European Patent Application No. 18723271.5 filed Jul. 16, 2024 (10 pages).

\* cited by examiner

BIOCOMPATIBLE POLYISOBUTYLENE-FIBER COMPOSITE MATERIALS AND METHODS

This application is a divisional of U.S. application Ser. No. 15/959,894, filed Apr. 23, 2018, which claims the benefit of U.S. Provisional Application No. 62/489,655 filed Apr. 25, 2017, the contents of which are herein incorporated by reference in their entirety.

FIELD

Embodiments herein relate to biocompatible composite materials. More specifically, embodiments herein relates to biocompatible polyisobutylene-fiber composite materials and related methods.

BACKGROUND

Many different implantable medical devices rely upon animal-derived or fully synthetic materials for their construction. As one example, the leaflets of heart valves have been formed from various materials, but are currently typically formed from animal tissues. Tissue valves, also known as biological or bioprosthetic valves, can be derived from animal tissue such as porcine (pig), bovine (cow) and equine (horse) models, and then fixed with a preserving solution before being mounted on a flexible frame to assist in deployment during surgery.

In comparison to mechanical valves, tissue valves offer avoidance of lifelong warfarin therapy to prevent the development of blood clots. However, a disadvantage of animal tissue valves is relatively poor durability compared to mechanical valves, with many requiring a re-operation in 10 to 20 years.

SUMMARY

Aspects herein relate to biocompatible polyisobutylene-fiber composite materials and related methods.

In a first aspect, a biocompatible composite material is included. The biocompatible composite material can include a network of fibers comprising one or more polymers to form a substrate and a continuous, interpenetrating polyisobutylene matrix that is non-porous and completely surrounds the electrospun fibers.

In addition to one or more of the preceding or following aspects, or in the alternative to some aspects, in a second aspect the network of fibers includes fibers oriented with a bias in a direction.

In addition to one or more of the preceding or following aspects, or in the alternative to some aspects, in a third aspect the network of fibers are electrospun fibers and are randomly oriented fibers.

In addition to one or more of the preceding or following aspects, or in the alternative to some aspects, in a fourth aspect the network of fibers comprise one or more of polyether-polyurethane copolymers (PE-PUR), high durometer polyisobutylene-polyurethane (PIB-PUR), polyamide, polyester, or linear polyethylene.

In addition to one or more of the preceding or following aspects, or in the alternative to some aspects, in a fifth aspect the fibers are disposed in a center of the polyisobutylene matrix.

In addition to one or more of the preceding or following aspects, or in the alternative to some aspects, in a sixth aspect the fibers are disposed biased towards an edge of the polyisobutylene matrix.

In addition to one or more of the preceding or following aspects, or in the alternative to some aspects, in a seventh aspect the biocompatible composite material is shaped as a prosthetic heart valve leaflet.

In addition to one or more of the preceding or following aspects, or in the alternative to some aspects, in an eighth aspect the composite material is substantially planar.

In addition to one or more of the preceding or following aspects, or in the alternative to some aspects, in a ninth aspect the network of fibers defines pores, wherein at least about 80% of the pores by volume are filled by the continuous, interpenetrating polyisobutylene matrix.

In addition to one or more of the preceding or following aspects, or in the alternative to some aspects, in a tenth aspect the composite is elastomeric.

In addition to one or more of the preceding or following aspects, or in the alternative to some aspects, in an eleventh aspect a method of manufacturing a biocompatible composite material is included. The method can include providing a network of electrospun fibers comprised of one or more thermoplastic polymers to form a substrate, adsorbing to the surface of the network of electrospun fibers a cross-linkable polyisobutylene composition comprising a polyisobutylene monomer, macromer, or polymer and a free radical initiator, and initiating cross-linking of the polyisobutylene polymer to create a continuous, interpenetrating thermoset polyisobutylene matrix that completely surrounds the electrospun fibers.

In addition to one or more of the preceding or following aspects, or in the alternative to some aspects, in a twelfth aspect the polyisobutylene polymer comprises methacrylate-endcapped telechelic PIB (PIB-DMA), acrylate-endcapped telechelic PIB (PIB-DA), monofunctional methacrylate-PIB (PIB-MA), or a star-PIB derivative having 3 or more branched side chains.

In addition to one or more of the preceding or following aspects, or in the alternative to some aspects, in a thirteenth aspect the free radical initiator comprises a photo-initiator.

In addition to one or more of the preceding or following aspects, or in the alternative to some aspects, in a fourteenth aspect at least one compound in the cross-linkable polyisobutylene composition comprises a cross-linkable vinylidene moiety.

In addition to one or more of the preceding or following aspects, or in the alternative to some aspects, in a fifteenth aspect the method can also include shaping the network of electrospun fibers into a prosthetic heart valve leaflet.

In addition to one or more of the preceding or following aspects, or in the alternative to some aspects, in a sixteenth aspect a method of manufacturing a biocompatible elastomeric composite material is included. The method can include providing a network of fibers comprised of one or more polymers to form a substrate, adsorbing to the surface of the network of fibers a cross-linkable polyisobutylene composition comprising a polyisobutylene (HR-PIB), maleic anhydride, and a free radical initiator and initiating cross-linking between the HR-PIB and maleic anhydride to form alternating PIB and maleic anhydride chains to create a continuous, interpenetrating thermoset polyisobutylene matrix that completely surrounds the electrospun fibers.

In addition to one or more of the preceding or following aspects, or in the alternative to some aspects, in a seventeenth aspect the polyisobutylene composition comprises PIB-diallyl, itaconic anhydride, and a free radical initiator.

In addition to one or more of the preceding or following aspects, or in the alternative to some aspects, in an eighteenth aspect the HR-PIB comprises a telechelic HR-PIB.

In addition to one or more of the preceding or following aspects, or in the alternative to some aspects, in a nineteenth aspect the HR-PIB comprises a monofunctional PIB.

In addition to one or more of the preceding or following aspects, or in the alternative to some aspects, in a twentieth aspect the method further includes the step of initiating a condensation reaction using a primary polyamine to create bis-maleimide bridges between cross-linked polyisobutylene and maleic anhydride chains.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following drawings, in which.

While embodiments are susceptible to various modifications and alternative forms, specifics thereof have been shown by way of example and drawings, and will be described in detail. It should be understood, however, that the scope herein is not limited to the particular embodiments described. On the contrary, the intention is to cover modifications, equivalents, and alternatives falling within the spirit and scope herein.

DETAILED DESCRIPTION

Many different implantable medical devices rely upon animal-derived or fully synthetic materials for their construction. As one example, the leaflets of heart valves have been formed from various materials, but are currently typically formed from animal tissues.

Aspects herein relate to fully synthetic materials that can be used for the construction of implantable medical devices. Fully synthetic materials as described herein can offer advantages including, but not limited to, high biocompatibility, little or no calcification of the material in vivo, tunable mechanical properties including elasticity, thin profiles for devices such as TAVR or mitral valves, and broad applications including use in other areas such as gastric, biliary, and urinary applications.

Figure 1:
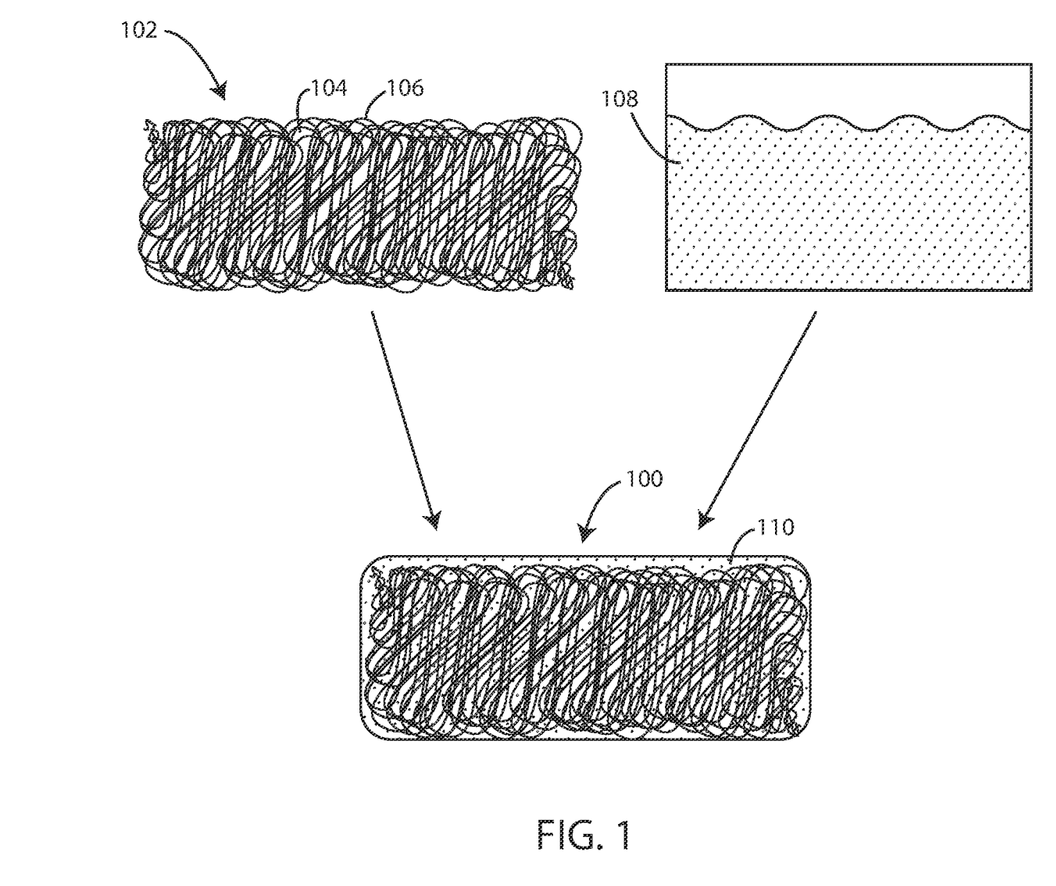
FIG. 1 is a schematic view of a biocompatible elastomeric composite material and components thereof including electrospun fibers and a polyisobutylene composition in accordance with various embodiments herein.

Referring now to FIG. 1, shown is a schematic of the biocompatible elastomeric composite material 100 in accordance with the embodiments herein. FIG. 1 shows a network of electrospun fibers 102 deposited as a substrate. The network of electrospun fibers can contain pores 104 of various shapes and sizes that result between adjacent fibers during the electrospinning process. The individual fibers 106 within the network can be oriented with a bias in a particular direction or the fibers can be randomly oriented. For example, in some embodiments individual fibers can be oriented with a bias parallel to, perpendicular to, or at a specific desired angle to a particular axis of significance in the article or device ultimately formed such as the major lengthwise axis, an axis of maximum strain, a particular axis of flexion, or the like.

The network of electrospun fibers 102 can be completely coated with a cross-linkable polyisobutylene composition 108, such as a flowable cross-linkable polyisobutylene composition. The polyisobutylene composition 108 can include at least a polyisobutylene polymer or derivative thereof and a free radical initiator, as discussed further below. The polyisobutylene composition 108 can be added to the network of electrospun fibers 102 by various methods, including spray coating, dip coating, or any other suitable method used to achieve complete coating of the network of electrospun fibers 102 and complete filling (or partially complete) of the pores 104 present therein.

Cross-linking of the polyisobutylene composition 108, such as with a photoinitiator, results in a continuous, interpenetrating thermoset polyisobutylene matrix 110 completely surrounding the network of electrospun fibers 102. The resulting composite fiber network and polyisobutylene matrix can create a nonporous biocompatible elastomeric composite material 100 as described herein. However, in some embodiments, such as where the polyisobutylene composition does not fully saturate spaces within the network of fibers, the resulting material can include both nonporous portions and porous portions (e.g., the network of fibers can remain porous in areas, if any, where the polyisobutylene composition does not penetrate). In various embodiments, the nonporous portions can be surface portions and the porous portions can be interior portions.

Figure 2:
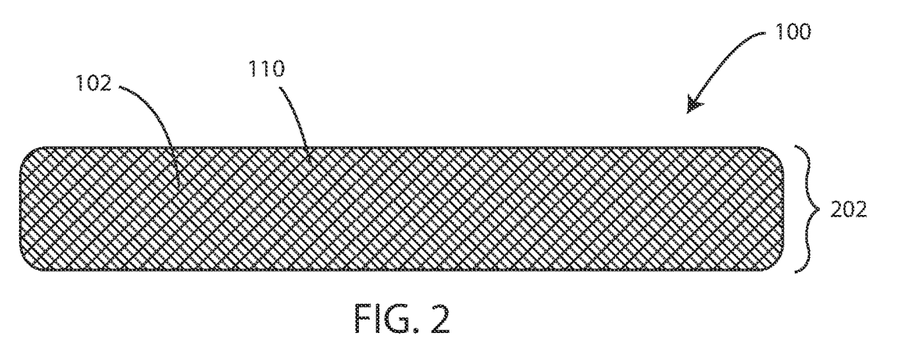
FIG. 2 is a schematic cross-sectional view of a biocompatible elastomeric composite material in according with various embodiments herein.
Figure 3:
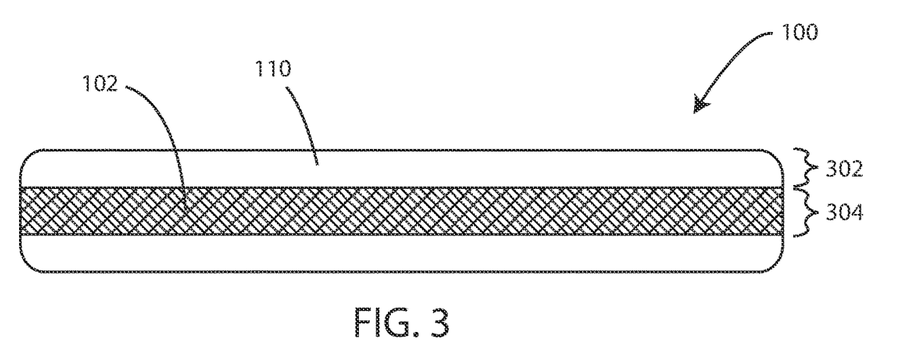
FIG. 3 is a schematic cross-sectional view of a biocompatible elastomeric composite material in according with various embodiments herein.
Figure 4:
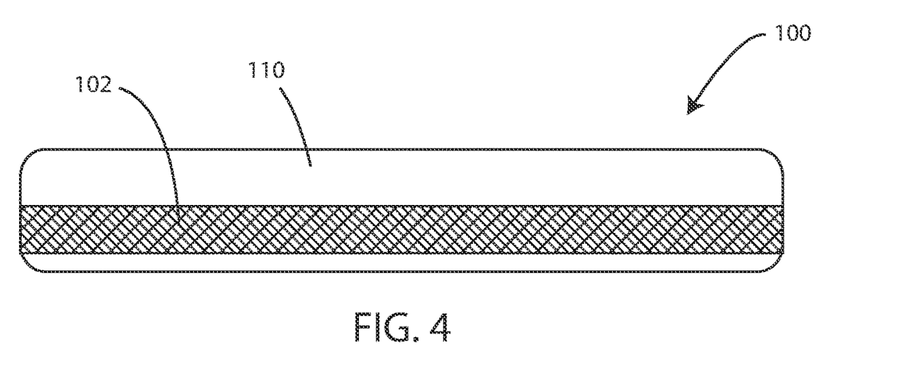
FIG. 4 is a schematic cross-sectional view of a biocompatible elastomeric composite material in according with various embodiments herein.

Referring now to FIGS. 2 through 4, shown are schematic cross-sectional representations of the biocompatible elastomeric composite material 100 in accordance with the embodiments herein. FIG. 2 shows the biocompatible elastomeric composite material 100 having a network of electrospun fibers 102 disposed essentially throughout the thickness 202 of the surrounding thermoset polyisobutylene matrix 110. The thickness 202 can vary depending on the specific application. However, in some embodiments, the thickness 202 can be about (or at least about) 50 μm, 75 μm, 100 μm, 125 μm, 150 μm, 175 μm, 200 μm, 225 μm, 250 μm, 275 μm, 300 μm, 400 μm, 500 μm, 1 mm, 2 mm, 3 mm, 5 mm or 10 mm. In some embodiments, the thickness 202 can be in a range wherein any of the foregoing numbers can serve as the upper or lower bound of the range, provided that the upper bound is greater than the lower bound.

FIG. 3 shows another example of the biocompatible elastomeric composite material 100 having a network of electrospun fibers 102 disposed in the center of the surrounding thermoset polyisobutylene matrix 110. In this view, there is a portion 304 of the composite material 100 that includes both the electrospun fibers 102 and the polyisobutylene matrix 110. There is also a portion 302 of the composite material 100 that includes the polyisobutylene matrix 110, but is substantially free of the electrospun fibers.

In some embodiments, the portion 304 that includes both the electrospun fibers 102 and the polyisobutylene matrix spans about (or at least about) 1, 5, 10, 20, 30, 40, 50, 60, 70, 80, 85, 90, 95, 98, 99, or 100 percent of the thickness of the composite material 100. In some embodiments, the portion 304 that includes both the electrospun fibers 102 and the polyisobutylene matrix spans a percentage of the thickness of the composite material in a range wherein any of the foregoing percentages can serve as the upper or lower bound of the range, provided that the upper bound is greater than the lower bound.

In some embodiments, the electrospun fibers can be centered within the composite with respect to the overall thickness thereof. However, in other embodiments, the electrospun fibers can be offset towards one side or the other of the composite creating an asymmetrical composite. FIG. 4 shows an example of a biocompatible elastomeric composite material 100 where the network of electrospun fibers 102 is disposed to one side the surrounding thermoset polyisobutylene matrix 110.

In still another embodiment, not shown, a portion of the fibers can extend outward beyond the polyisobutylene matrix.

In some embodiments, the density of the fibers can be the same throughout the composite with respect to the thickness, the length or the width of the composite. However, in other embodiments, the density of the fibers can vary and be denser in some places and less dense in others.

Polymeric Fiber Network Substrates Polymeric fiber network substrates described herein can be formed of various polymeric materials. The fibers can include a polymeric material such as a polymer, or a blend of polymers. Polymers herein can include homopolymers, copolymers, terpolymers, and the like. A "monomer" is a polymerizable molecule. Typically, the polymeric materials comprise polymer molecules having a median number of monomers that numbers in the tens (10 to 99), in the hundreds (100 to 999), in the thousands (1,000 to 9,999), or in the tens of thousands (10,000 to 99,999) as well as a mixture of polymers having different median numbers of monomers. The polymeric materials can comprise polymer molecules having a median number of monomers that is 100,000 or more.

Polymeric fiber network substrates described herein can be created from polymers that are cross-linked or uncross-linked, linear or branched, natural or synthetic, thermoplastic or thermosetting, and may be biostable, biodegradable, bioabsorbable, biodisintegrable, or dissolvable. Polymeric fiber network substrates described herein can specifically include those exhibiting hydrolytic stability in the context of long-term (chronic) implantation.

Polymers used to create the polymeric fiber network substrates herein can include those that are capable of being electrospun. Exemplary polymers can include, but are not limited to, polyether-polyurethane (PE-PUR) copolymers, high durometer polyisobutylene-polyurethane (PIB-PUR), polyamides such as nylons, polyesters, polyisobutylene (PIB), poly(ethylene oxide), polyethylene, poly(styrene-block-isobutylene-block-styrene (SIBS), polypropylene, polystyrene, polyvinylchloride, poly(styrene) polyurethanes, polyvinylidene difluoride, poly(methyl methacrylate), polyethylene glycol, polyanilines, polypyrroles, polythiophenes, polyphenols, polyacetylenes, polyphenylenes, polyacrylonitriles, polylactic acids, polycaprolactone, polyglycolides, polyvinyl acetates, cellulose acetate and copolymers including one or more of these. Polymers can also include biological polymers such as chitosan, proteins, carbohydrates, and the like.

In some embodiments, polymers used to create the polymeric fiber network herein are cross-linked. In other embodiments, polymers used to create the polymeric fiber network herein are not cross-linked.

The polymeric fiber network substrate can have various thicknesses. In some embodiments, the polymeric fiber network substrate can have a thickness of about (or at least about) 50 µm, 75 µm, 100 µm, 125 µm, 150 µm, 175 µm, 200 µm, 225 µm, 250 µm, 275 µm, 300 µm, 400 µm, 500 µm, 1 mm, 2 mm, 3 mm, 5 mm or 10 mm. In some embodiments, the thickness can be in a range wherein any of the foregoing numbers can serve as the upper or lower bound of the range, provided that the upper bound is greater than the lower bound.

Fiber Formation

The polymeric fibers herein can be formed in various ways including, but not limited to, electrospinning, electrospraying, spinning, centrifugal spinning (force spinning), drawing, template synthesis, phase separation, melt spinning, melt-blowing, self-assembly and the like. In some embodiments, the polymeric fibers can be a woven or non-woven polymeric fabric.

In some examples, the polymeric fibers can specifically be formed through an electrospinning (or electrostatic fiber formation or electrospraying) process. Electrospinning is a fiber production method which uses electric force to draw charged threads of polymer solutions or polymer melts. When a sufficiently high voltage is applied to a liquid droplet, the body of the liquid becomes charged, and electrostatic repulsion counteracts the surface tension and the droplet is stretched. At a critical point, a stream of liquid erupts from the surface. This point of eruption is known as the Taylor cone. If the molecular cohesion of the liquid is sufficiently high, stream breakup does not occur and a charged liquid jet is formed. As the jet dries in flight, the mode of current flow changes from ohmic to convective as the charge migrates to the surface of the fiber. The jet is then elongated by a whipping process caused by electrostatic repulsion initiated at small bends in the fiber, until it is finally deposited on the grounded collector. The elongation and thinning of the fiber resulting from this bending instability leads to the formation of substantially uniform fibers with nanometer-scale diameters.

The two principal parameters that control behavior of the Taylor cone are the viscosity and voltage at the nozzle. Exemplary methods of creating ultra-thin fibers for use in creating a fiber network involve electro-spinning. Electrospinning methods are described in Shin, Hohman, Brenner, and Rutledge, "Experimental Characterization of electrospinning: the electrically forced jet and instabilities", Polymer 42, 9955-9967, (2001), incorporated herein by reference in its entirety. Fibers that are micrometers in diameter can be created by melt spinning or gel spinning, i.e., they are formed out of a gel or a molten melt.

One exemplary method of depositing the fiber network, is to use a process referred to as flow-limited field-injection electrostatic spraying (FFESS). FFESS is a form of electrospraying which offers a very high degree of control over shape and flow regimes, and which allows spinning a fiber-network on top of a medical device, such as an endoprosthesis, with a glass spray nozzle. The nozzle generates a charge at the liquid meniscus that enables successful electrospray. The two principal differences between conventional electro-spraying (CES) and FFESS are first that FFESS sprays a polymer/solvent solution from a smooth glass capillary whereas CES uses a metal hypodermic needle, and second that FFESS uses a sharpened tungsten needle inside the capillary, whereas CES has no analogous structure. The overall effect of the FFESS apparatus is to improve jet stability and uniformity of the polymer sprayed by FFESS relative to that from CES.

Using the FFESS method for electro-spinning creates a fiber network in which the one or more fibers have a highly controlled fiber diameter. In particular, as would be understood by one of ordinary skill in the art, by controlling the voltage, flow-rate, concentration of polymer in the spray fluid, the viscosity of the spray fluid, and the distance of the nozzle from the surface of the underlying structure (e.g., a mold or a medical device frame, or a pocket within a medical device frame), the diameter of the fibers formed during the spinning process can be controlled. For exemplary descriptions of the various factors, see, e.g., "Electrostatic Spinning and Properties of Ultrafine Fibers", Rutledge, et al., National Textile Center Annual Report, M01-D22, (November 2001), incorporated herein by reference. It is also consistent with the fiber network that the diameter of the fibers can be changed during deposition.

A further advantage of FFESS is thus that, because of the high degree of control of the fiber diameter, if the weight of the fiber network as well as the density of the polymer material for a given fiber diameter are known, the total surface area of the network can be precisely calculated. Thus, the surface area of a fiber of diameter d, and of length l, assuming a uniform perfectly cylindrical constant cross-section along its length, is $\pi dl$, ignoring contributions from the ends of the fibers. FFESS is further described in "Controlling surface nano-structure using flow-limited field-injection electrostatic spraying (FFESS) of poly(d,l-lactide-co-glycolide)", Berkland, Pack, and Kim, Biomaterials, 25: 5649-5658, (2004) and U.S. Patent Application Publication No. 2004/0022939, both of which are incorporated herein by reference in their entirety.

Solvents used during the electrospinning process can affect various aspects such as fiber morphology. Solvents used can include, but are not limited to, dichloromethane, chloroform, methanol, tetrahydrofuran, ethyl acetate, ethanol, methyl ethyl ketone, dichloroethane, water, dimethylformamide, and combinations including one or more of these. In some examples, the solution conductivity can be manipulated in order to impact fiber diameter and morphology. By way of example, various salts (including but not limited to sodium chloride and phosphate salts) can be added with the solvent in order to change the solution conductivity.

Figure 5:
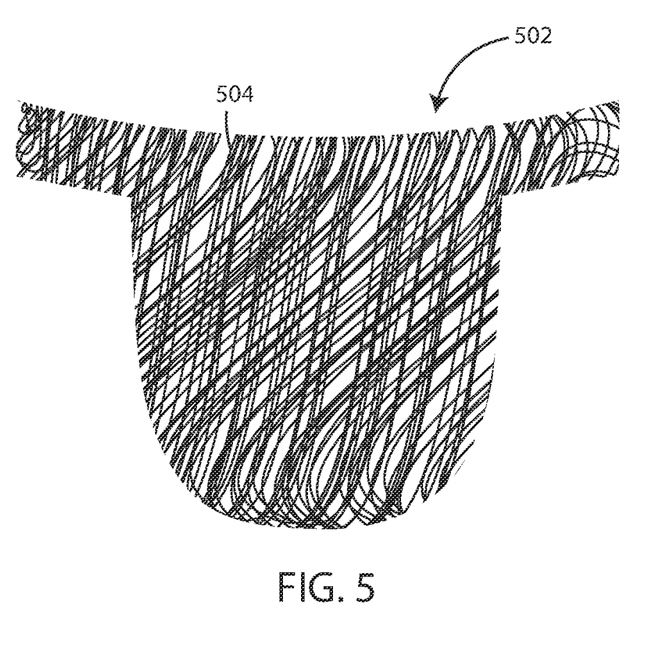
FIG. 5 is schematic view of a polymeric fiber network substrate in the shape of a valve leaflet.
Figure 6:
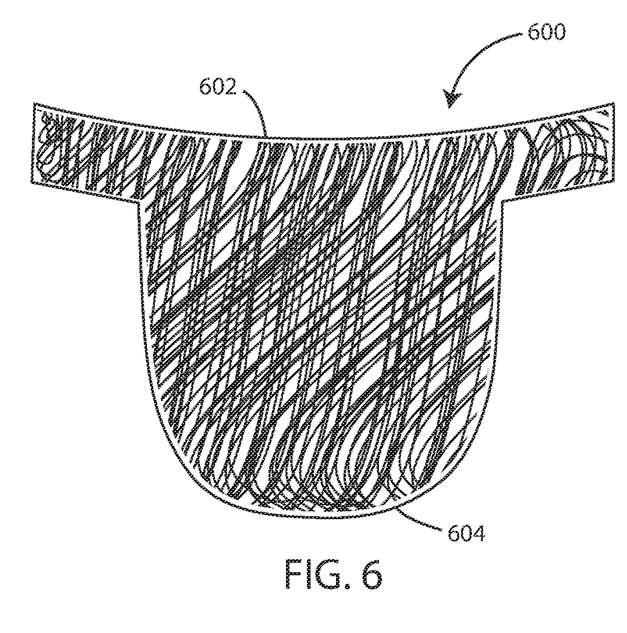
FIG. 6 is schematic view of a biocompatible elastomeric composite material in the shape of a valve leaflet.

In some embodiments, the fiber network can be deposited directly onto a structure or form having the desired shape of the final product. For example, in some embodiments, the fiber network can be deposited onto a mold or a portion thereof having a shape of a prosthetic heart valve leaflet as seen in FIGS. 5-6. In some embodiments, the fiber network can be deposited onto a build surface or plate that is substantially flat and the desired form of the fiber network can be controlled by manipulating the spray stream and/or the device creating the spray stream.

Beyond electrospinning, it will be appreciated that polymeric fiber networks herein can be deposited and/or formed into components of a biocompatible material in other ways. For example, in some examples, fibers can be woven. In some examples fibers can be woven to form a fibrous matrix forming at least part of a biocompatible material.

Diameters of the polymeric fibers used herein can be greater than about 5, 10, 20, 30, 50, 100, 150, 200, 250, 500, 750, or 1000 nanometers. In some examples the diameter of the polymeric fibers herein can be greater than about 1, 2, 3, 4, 5, 6, 7, or 8 micrometers. Diameters of the polymeric fibers used herein can be less than about 20, 18, 16, 14, 12, 10, 8, 6, 4, 2 or 1 micrometer. In some examples, diameters of the polymeric core of fibers used herein can be less than about 1000, 900, 800, 700, 600, 500, 400, 200, 100, or 50 nanometers. Diameters of the polymeric fibers used herein can be within a range wherein any of the foregoing numbers can serve as the lower or upper bound of the range, provided that the lower bound is less than the upper bound. In some examples, the average diameter of the polymeric core can be from about 10 nanometers to about 10 micrometers.

The fiber portion of the composite material can be greater than about 5, 10, 15, 20, 25, 30, 35, 40, 45, 50, 55, 60, 65, 70, 75, 80, 85, 90, or 95 weight percent. In some embodiments, the fiber portion of the composite material can be in a range wherein any of the foregoing numbers can serve as the upper or lower bound of the range provided that the upper bound is greater than the lower bound.

As references above, the fibers (fiber substrate or fiber mat) can include a substantial number of pores. However, when combined with the polyisobutylene composition that is later turned into an interpenetrating polyisobutylene matrix, the pores are filled by the polyisobutylene material. The amount of the pores in the fiber substrate that are filled by the polyisobutylene material can vary depending on various factors including the amount of the polyisobutylene material used compared with the amount of the fibers, how long the polyisobutylene material is allowed to penetrate the pores before undergoing a chemical reaction such as polymerization and/or cross-linking, the initial viscosity of the polyisobutylene material and the like. However, in various embodiments, about (or at least about) 10, 20, 30, 40, 50, 60, 70, 80, 90, 95, 98, 99, or 100 percent of the pores (as measured based on volume) are filled by the polyisobutylene matrix in the composite material. In some embodiments, the percentage of the pores that are filled can be in a range wherein any of the foregoing percentages can serve as the upper or lower bound of the range, provided that the upper bound is greater than the lower bound.

Polyisobutylene Compositions

In accordance with the embodiments herein, a polyisobutylene composition, which can include at least a polyisobutylene (monomer such as isobutylene, macromer, or polymer) or a derivative thereof and a free radical initiator, can be polymerized and/or cross-linked to form a continuous, interpenetrating polyisobutylene matrix that is nonporous and completely surrounds an electrospun fiber network. In some embodiments, the polyisobutylene composition can be a polyisobutylene fluid composition. In some embodiments, the polyisobutylene composition can be a flowable polyisobutylene fluid composition. In some examples the continuous, interpenetrating polyisobutylene matrix is either thermoplastic or thermoset. In some examples the continuous, interpenetrating polyisobutylene matrix is cross-linked and in other examples it is not cross-linked.

Pure homopolymeric polyisobutylene can be formed by the polymerization of isobutylene monomers having the chemical formula $-[C(CH_3)_2CH_2]_n-$, where n can be any number between 10 and 100,000 or more. Derivatives of polyisobutylene suitable for use herein can include those having symmetrical or asymmetrical functional end groups at the termini of a polyisobutylene chain. In some embodiments, the functional end groups can include, but not be limited to acrylate or methacrylate. In some embodiments, the functional end groups can include exo-olefinic groups. An exo-olefinic group for use herein can have the following formula:

where R is the polyisobutylene-based polymer chain. In some embodiments, the exo-olefinic group can be methyl vinylidene. To obtain even higher cross-link densities within the polyisobutylene matrix, in some embodiments "star" derivatives of polyisobutylene (star-PIB) can also be used. A star-PIB as used herein can be a derivative of polyisobutylene having three or more branches of functionalized polyisobutylene chains available for cross-linking.

The polyisobutylene compositions herein can include polyisobutylenes and derivatives thereof, including, but not limited to acrylate or methacrylate end-capped telechelic polyisobutylene, monofunctional polyisobutylene methacrylate, highly reactive polyisobutylene (HR-PIB), highly reactive telechelic polyisobutylene, diallyl polyisobutylene, monofunctional highly reactive polyisobutylene, or any other polyisobutylene derivative in accordance with the embodiments herein. As used herein, the term "telechelic" refers to any polymer that contains two or more reactive end groups, where the reactive end groups can be used in cross-linking to promote polymerization of the polyisobutylene matrix.

In some embodiments, polyisobutylenes and derivatives thereof consistent with the embodiments herein can be viscous compositions at room temperature and can range in molecular weight from 1,000 to 10,000 grams per mole (g/mol). In some embodiments, polyisobutylenes and derivatives thereof can have a molecular weight anywhere from 2,000 to 3,000 g/mol. In some embodiments, the polyisobutylenes and derivatives thereof used herein can have a molecular weight of less than or equal to 1,000, 2,000, 3,000, 4,000, 5,000, 6,000, 7,000, 8,000, 9,000, or 10,000 g/mol, or in a range between any of the foregoing numbers.

The polyisobutylene compositions herein can have viscosities ranging from 1,000 centipoise (cP) to 25,000 cP at room temperature. In some embodiments, the polyisobutylene compositions can have a viscosity of 10,000 cP at room temperature. In some embodiments, polyisobutylene compositions can have a viscosity of less than or equal to 25,000, 20,000, 15,000, 10,000, 8,000, 7,500, 5,000, 4,000, 3,000, 2,000, or 1,000 cP at room temperature. Viscosity of the polyisobutylene compositions used herein can be within a range wherein any of the foregoing numbers can serve as the lower or upper bound of the range, provided that the lower bound is less than the upper bound.

Many suitable free radical initiators can be used in the polyisobutylene compositions herein and can include, but are not limited to, thermal, ambient redox, and photo free radical initiators. Free radical initiators can include, but are not limited to, organic free radical initiators such as organic peroxides and azo compounds, or inorganic free radical initiators such as inorganic peroxides Other free radical initiators herein can include photoinitiators. Examples of photoinitiators suitable for use herein include compounds from the α-hydroxyketone class of compounds, such as 1-[4-(2-hydroxyethoxy)-phenyl]-2-hydroxy-2-methyl-1-propane-1-one (known commercially as Irgacure® 2959, BASF, Florham Park, NJ). Other examples of suitable photoinitiators include those from the family of α-amino ketones, acyl phosphine oxides, or benzophenones.

Other reagents for use in radical polymerization of the polyisobutylene polymers used herein can include maleic anhydride, itaconic anhydride, and the like.

Polyisobutylene compositions herein, after polymerization and/or cross-linking, can specifically exhibit hydrolytic stability in the context of long-term (chronic) implantation.

Methods of Making Biocompatible Elastomeric Composite Materials

Biocompatible elastomeric composite materials embodied herein can be created using various techniques. In some embodiments, electrospun fibers can be formed first into a substrate (with or without a specific shape) and then a polyisobutylene fluid can be applied to the substrate (through spraying, dip coating, brush coating, immersion, or the like) followed by cross-linking and/or polymerization. In some embodiments, the electrospun fiber is deposited onto a structure and the polyisobutylene composition is spray coated onto the network of electrospun fibers. London forces between adjacent PIB polymers and fibers provide enough attraction to allow the polyisobutylene composition to take the shape of the underlying structure.

However, in some embodiments, electrospun fibers are first sprayed into a volume of polyisobutylene fluid followed by cross-linking and/or polymerization of the polyisobutylene fluid.

A particular shape can be imparted to the composite in many different ways. In some embodiments, a form or mold having a cavity with the desired end shape can be used. In such a case, the electrospun fibers can be deposited into the form or mold and assume the shape of the cavity into the form or mold. Then a polyisobutylene fluid can be added into the form or mold followed by cross-linking and/or polymerization.

Alternatively, the polyisobutylene fluid can be disposed into the form or mold first and then the electrospun fibers can be deposited into the polyisobutylene fluid. In some cases, the electrospun fibers can be deposited onto a build plate or base plate or other surface (such as a flat surface) that does not become part of the finished structure. The electrospun fibers can be deposited in a manner so that a shape is formed either through movement of the portion of a device emitting the electrospray or another component of the spraying apparatus. Then the polyisobutylene fluid can be applied onto the deposited electrospun fibers (through various techniques) followed by cross-linking and/or polymerization. The build plate or base plate can be separated from the electrospun fibers either before or after the polyisobutylene fluid is applied onto the electrospun fibers.

In still other cases, the electrospun fibers can be deposited onto a material that does become part of the finished structure such as an underlying material or support layer.

In some embodiments, a particular shape can be created by first forming the composite into a substantially planar layer and then cutting the planar layer to the desired shape and dimensions. However, while not intending to be bound by theory, such a cutting step after composite formation can be less desirable for some applications as it is more likely to result in cut-ends of the electrospun fiber exposed on the surface of the composite. As such, in some embodiments herein, the composite lacks cut-ends of electrospun fibers on the surfaces of the composite. In some embodiments herein, the electrospun fibers are completely covered by the polyisobutylene material on the surfaces of the composite.

Biocompatible elastomeric composite materials as embodied herein can be created through various free radical polymerization reactions. In some embodiments, creating a thermoset polyisobutylene matrix around a network of electrospun fibers can include using a polyisobutylene composition including a telechelic polyisobutylene and a free radical initiator, such as a photoinitiator. In one example, telechelic polyisobutylene-dimethacrylate (PIB-DMA), a telechelic polyisobutylene having a methacrylate group on each end, is mixed with the photo initiator 1-[4-(2-hydroxyethoxy)-phenyl]-2-hydroxy-2-methyl-1-propane-1-one (known commercially as Irgacure® 2959, BASF, Florham Park, NJ). The photo initiator can be activated by illuminating the polyisobutylene composition with a UV/VIS light source at the appropriate wavelength (approximately 260-290 nm, with an absorption maximum at 276 nm for Irgacure® 2959). PIB-DMA can react with Irgacure® 2959 and form cross-links to other PIB-DMA polymers to form a thermoset polyisobutylene matrix completely surrounding the polymeric fiber network substrate.

In some embodiments, creating a thermoset polyisobutylene matrix around a network of electrospun fibers can include using a polyisobutylene composition including a highly reactive polyisobutylene (HR-PIB), an anhydride such as maleic anhydride or itaconic anhydride, and a free radical initiator. In some embodiments, the HR-PIB can include vinylidene, or exo-terminated, end groups at either end of the PIB chain. In one example, a HR-PIB such as exo-olefin (methyl vinylidene)-terminated PIB can be mixed with maleic anhydride and a free radical initiator (R') to yield a network of polymerized chains having alternating maleic anhydride and vinylidene PIB endgroups. Suitable free radical initiators for use herein are discussed above.

In some embodiments, creating a thermoset polyisobutylene matrix around a network of electrospun fibers can include using a polyisobutylene composition including a monofunctional HR-PIB, having only one exo-terminated end group, and maleic anhydride. For example, monofunctional HR-PIB can be radically polymerized with maleic anhydride to yield chains having alternating PIB and maleic anhydride groups. In some embodiments, the alternating PIB and maleic anhydride groups can be further cross-linked via a condensation reaction using a diamine to create bis-maleimide bridges between the chains. Examples of suitable diamines, including primary polyamines having the general formula $H_2N-CH_2-[CH_2]_n-CH_2-NH_2$, where n can be any number greater than 1, and can include at least putrescine, cadaverine, and hexamethylenediamine.

Applications

The biocompatible elastomeric composite materials described herein can be used in many applications including, but not limited to, medical and biological applications. In some embodiments, the biocompatible elastomeric composite materials can be used as the basis for prosthetic heart valve leaflets.

In some embodiments, a polymeric fiber network substrate can be formed into the shape of a valve leaflet. Referring now to FIG. 5, a polymeric fiber network substrate 502 can be formed into the shape of a valve leaflet. The polymeric fiber network substrate 502 can include a plurality of fibers 504.

Referring now to FIG. 6, a prosthetic heart valve leaflet 600 is shown comprised of biocompatible elastomeric composite materials in accordance with the embodiments herein. Prosthetic heart valve leaflet 600 can include a root portion 602 and an edge portion 604. In some embodiments, the prosthetic heart valve leaflet 600 can be formed from a biocompatible elastomeric composite material as described herein, where the network of electrospun fibers is uniformly distributed throughout the valve leaflet. In other embodiments, the prosthetic heart valve leaflet 600 can be formed from a biocompatible elastomeric composite material as described herein, where the network of electrospun fibers is distributed as a gradient, the concentration of electrospun fibers being highest near root portion 602 and the concentration of electrospun fibers being lowest near edge portion 604.

The thickness of biocompatible elastomeric composite material described herein can be tuned depending on the application. For example, biocompatible elastomeric composite material used for prosthetic heart valve leaflet 600 can be designed such that the maximum thickness of the leaflet is 100 µm or less. In some embodiments, prosthetic heart valve leaflet 600 can be designed having a decreasing thickness in a direction extending from root portion 602 towards edge portion 604. The decreasing thickness in a direction extending from root portion 602 towards edge portion 604 can be achieved through a decreasing thickness in the network of electrospun fibers present in prosthetic heart valve leaflet 600 or through a decreasing thickness in the thermoset polyisobutylene matrix, or both.

While FIGS. 5-6 show a particular example of (and configuration for) a heart valve leaflet, it will be appreciated that many other physical configurations of heart valve leaflets are contemplated herein as well as valves other than heart valves. FIGS. 5-6 show a two-dimensional layout for a valve leaflet that would later be sewn (or otherwise attached) to a frame. But, other types of valve leaflet configurations are also included herein. For example, heart valve leaflets that are initially formed in their final three-dimensional shape are also included herein. Heart valve leaflets that are formed integrally with a frame are also included herein.

It will be appreciated that biocompatible elastomeric composite materials described herein can used to form various medical devices and/or portions thereof. In some embodiments, the biocompatible elastomeric composite material described herein can be used in in vivo environments where long-term implantation of an elastic material having anti-thrombogenic and anti-calcification properties is required.

In some embodiments, the biocompatible elastomeric composite material described herein can be used in in vivo environments to sequester encapsulated material within a body cavity or other in vivo region of the body.

Figure 7:
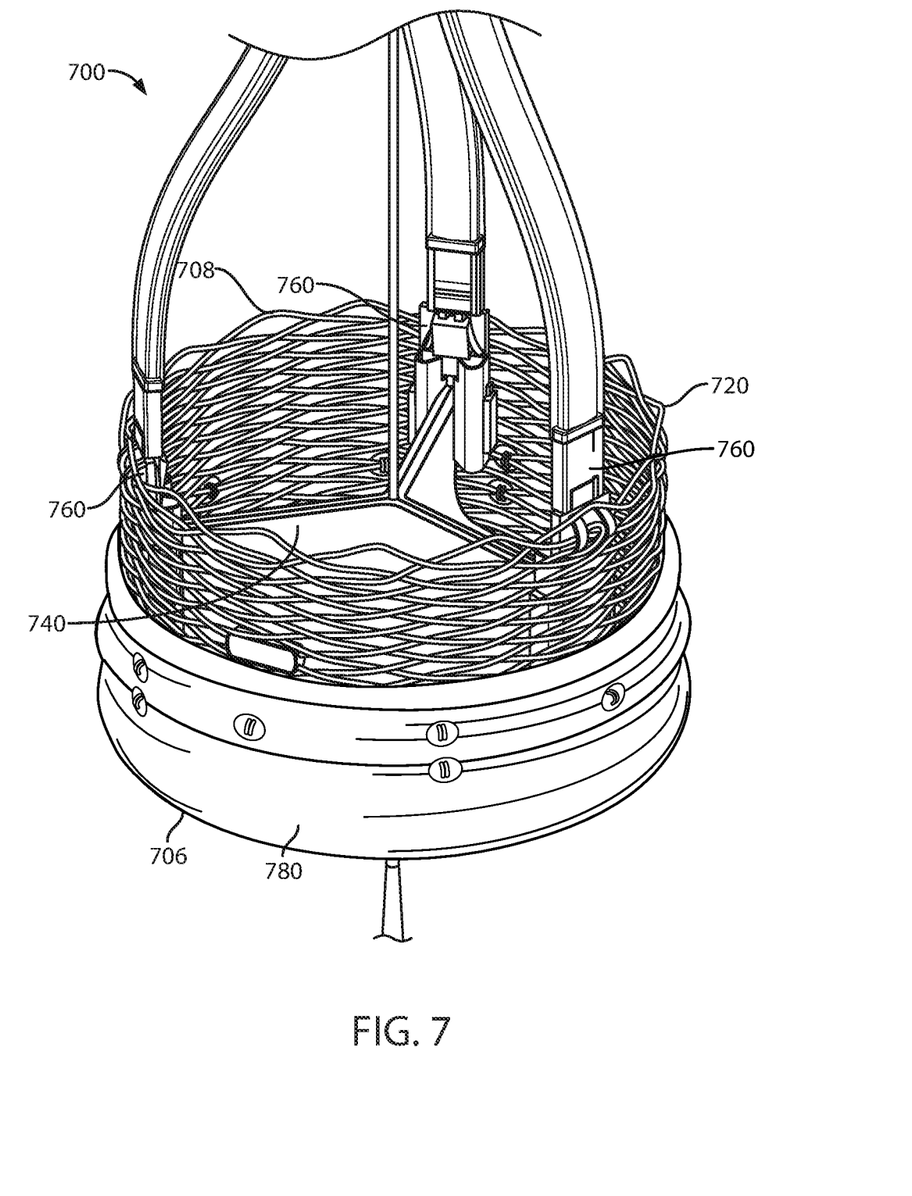
FIG. 7 is a schematic view of a prosthetic heart valve in accordance with various embodiments herein.

As merely one specific example, the biocompatible elastomeric composite material described herein can be used to form a prosthetic heart valve or a portion thereof. FIG. 7 provides a schematic view of the prosthetic heart valve 700 of FIG. 7 having inflow end 706 and an outlet end 708. Prosthetic heart valve 700 has a substantially tubular body 720, a plurality of leaflets 740, anchor elements 760 and a tubular seal 780. The tubular body 720 can be a radially expandable member, e.g. annular frame or stent, having an annular cavity. As shown in FIG. 7, the heart valve 700 can have three heart valve leaflets 740 coupled to the tubular body 720 within the annular cavity. Each leaflet 740 can be secured to an adjacent leaflet 740 and to the expanding tubular body by stitches. Three anchor elements 760 positioned within the annular cavity of the tubular body can each secure the heart valve leaflets 740 to the tubular body 720. Each anchor elements 760 can be coupled to the tubular body 720 with an anchoring element 760 and also be coupled to the leaflets 740 with a clamping element. The tubular seal 780 can be disposed about at least a portion of the tubular body 720. In particular, the tubular seal 780 can have an inflow end portion 706 secured to bottom edges of the plurality of leaflets 740 and have an outflow end portion 708 disposed about an outer surface of the tubular body 720 to restrict blood flow around the leaflets 740.

In use, prosthetic heart valve 700 is implanted (e.g., surgically or through transcatheter delivery) in a mammalian heart. The edge portions of the polymeric leaflets 740 move into coaptation with one another in a closed position to substantially restrict fluid from flowing past prosthetic heart valve 700 in a closed position. The edge portions of the leaflets 740 move away from one another to an open position permitting fluid to flow past prosthetic heart valve 700. Movement of the leaflets 740 between the closed and open positions can substantially approximate the hemodynamic performance of a healthy natural valve.

Prosthetic heart valve 700 can be made of various materials. Synthetic materials of the prosthetic heart valve 700 can include polymeric materials, metals, ceramics, and combinations thereof. In various embodiments herein, however, the leaflets 740 can be formed of a biocompatible composite material as described herein.

The embodiments described herein are not intended to be exhaustive or to limit the invention to the precise forms disclosed in the following detailed description. Rather, the embodiments are chosen and described so that others skilled in the art can appreciate and understand the principles and practices. However, it should be understood that many variations and modifications may be made while remaining within the spirit and scope herein.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

The invention claimed is:

1. A biocompatible composite material comprising:
a network of fibers comprising one or more polymers to form a substrate; and
a continuous polyisobutylene matrix that is non-porous and completely surrounds fibers of the network of fibers;
wherein the continuous polyisobutylene matrix comprises polymerized methacrylate-endcapped telechelic PIB (PIB-DMA), acrylate-endcapped telechelic PIB (PIB-DA), monofunctional methacrylate-PIB (PIB-MA), or a star-PIB derivative having 3 or more branched side chains.

2. The biocompatible composite material of claim 1, wherein the network of fibers includes fibers oriented with a bias in a direction.

3. The biocompatible composite material of claim 1, wherein the network of fibers are electrospun fibers and are randomly oriented fibers.

4. The biocompatible composite material of claim 1, wherein the network of fibers comprise one or more of polyether-polyurethane copolymers (PE-PUR), high durometer polyisobutylene-polyurethane (PIB-PUR), polyamide, polyester, or linear polyethylene.

5. The biocompatible composite material of claim 1, wherein the fibers are disposed in a center of the continuous polyisobutylene matrix.

6. The biocompatible composite material of claim 1, wherein the biocompatible composite material is substantially planar.

7. The biocompatible composite material of claim 1, the network of fibers defining pores, wherein at least about 80% of the pores by volume are filled by the continuous polyisobutylene matrix.

8. The biocompatible composite material of claim 1, the network of fibers defining pores, wherein at least about 99% of the pores by volume are filled by the continuous polyisobutylene matrix.

9. The biocompatible composite material of claim 1, wherein the biocompatible composite material is elastomeric.

10. The biocompatible composite material of claim 1, the network of fibers and the continuous polyisobutylene matrix comprising a prosthetic heart valve leaflet.

11. The biocompatible composite material of claim 10, the prosthetic heart valve leaflet having a decreasing thickness in a direction extending from a root portion towards an edge portion.

12. The biocompatible composite material of claim 11, comprising a decreasing thickness in the network of fibers present in the prosthetic heart valve leaflet in a direction extending from the root portion towards the edge portion.

13. The biocompatible composite material of claim 1, comprising a first portion including both the fibers and the continuous polyisobutylene matrix and a second portion including the continuous polyisobutylene matrix, but not the fibers.

14. A biocompatible composite material comprising:
a network of fibers comprising one or more polymers to form a substrate; and
a continuous polyisobutylene matrix that is non-porous and completely surrounds fibers of the network of fibers;
wherein the continuous polyisobutylene matrix comprises a reaction product of a cross-linkable polyisobutylene composition comprising a polyisobutylene (HR-PIB), maleic anhydride, and a free radical initiator.

15. The biocompatible composite material of claim 14, wherein the HR-PIB comprises a telechelic HR-PIB.

16. The biocompatible composite material of claim 14, wherein the HR-PIB comprises a monofunctional PIB.

* * * * *